United States Patent

Koh

[11] Patent Number: 6,068,754
[45] Date of Patent: May 30, 2000

[54] MULTI-TANK GEL DEVELOPING APPARATUS AND METHOD

[76] Inventor: Francis H. Koh, 7809 Bradley Blvd., Bethesda, Md. 20817

[21] Appl. No.: 09/102,055

[22] Filed: Jun. 22, 1998

Related U.S. Application Data

[60] Provisional application No. 60/083,065, Apr. 27, 1998.

[51] Int. Cl.$^7$ ................... G01N 27/26; G01N 27/447
[52] U.S. Cl. .................... 204/613; 204/456; 204/462; 204/466; 204/606; 204/616; 134/182; 134/183; 118/429; 118/500
[58] Field of Search .................. 204/462, 463, 204/461, 612, 613, 606, 456, 466, 616; 134/183, 182; 435/40.52; 118/424, 500

[56] References Cited

U.S. PATENT DOCUMENTS

| | | |
|---|---|---|
| 898,354 | 2/1908 | Gilbert . |
| 3,118,829 | 1/1964 | Raymond . |
| 3,168,100 | 2/1965 | Rich . |
| 3,930,880 | 1/1976 | Hoefer ..................... 204/613 |
| 4,357,174 | 11/1982 | Rushbrook et al. ............. 134/10 |
| 4,360,418 | 11/1982 | Golias . |
| 4,391,689 | 7/1983 | Golias . |
| 4,622,076 | 11/1986 | Ling . |
| 4,630,625 | 12/1986 | Capella et al. . |
| 4,635,791 | 1/1987 | Jackson et al. ................ 206/210 |
| 4,702,266 | 10/1987 | Chu . |
| 4,705,056 | 11/1987 | Chu . |
| 4,707,233 | 11/1987 | Margolis . |
| 4,750,506 | 6/1988 | Olexa ..................... 134/201 |
| 4,844,782 | 7/1989 | Hagerlid et al. . |
| 5,064,768 | 11/1991 | Ebata et al. . |
| 5,073,504 | 12/1991 | Bogen . |
| 5,097,129 | 3/1992 | de Vries et al. . |
| 5,112,461 | 5/1992 | Barnes . |
| 5,112,957 | 5/1992 | Pollard ..................... 204/462 |
| 5,439,649 | 8/1995 | Tscung et al. . |
| 5,458,749 | 10/1995 | Stone et al. . |
| 5,567,585 | 10/1996 | Caetano-Annolles et al. ..... 204/462 X |
| 5,776,684 | 7/1998 | Chirikjian et al. ............. 435/6 |

FOREIGN PATENT DOCUMENTS

| | | |
|---|---|---|
| 2164584 | 6/1985 | United Kingdom . |
| WO 93/13410 | 12/1992 | WIPO . |

OTHER PUBLICATIONS

*Novex Electrophoresis Product Catalog,* 98–99, p. 67, No date available.

Primary Examiner—Jill Warden
Assistant Examiner—John S. Starsiak, Jr.

[57] ABSTRACT

The claimed multi-tank gel developing apparatus and method comprises of two inner tanks within one outer tank to develop multiple electrophoresis gels simultaneously. The two inner tanks have openings along the edges of the walls to allow free circulation of solutions between the inner and outer tanks. The solution maybe exchanged by lifting out the inner tanks which retains the gels inside while the solution drains out. Once the solution in the outer tank has been exchanged, the inner tanks can be re-immersed into the outer tank. Furthermore, the inner tanks have detachable bases to facilitate transfer of the gels after development. This claimed apparatus allows for efficient development of electrophoresis gels by minimizing the direct handling of the gels thereby avoiding unwanted damages often incurred by conventional manually developing methods and apparatuses. The multi-tank apparatus can accommodate various gel compositions and sizes.

7 Claims, 2 Drawing Sheets

MULTI-TANK GEL DEVELOPING APPARATUS AND METHOD

This application claims benefit of provisional application Ser. No. 60/083,065 filed Apr. 27, 1998.

BACKGROUND OF THE INVENTION

By the use of gel electrophoresis methods and devices, various molecular species such as proteins, and deoxyribonucleic acids (DNA) can be separated by charge and molecular weight. The gels are in the form of either slab or tube and are developed by methods involving silver stains or fluorescent dyes to visualize the migration of various species. The staining or dyeing processes require the exchange of solutions according to different stages of development which usually involves fixing, staining, and rinsing. The gels being composed of polyacrylamide or agarose are fragile and require extreme care when developing. As to avoid tearing or damaging the gels, efforts are made to avoid direct hand contact of the gels. Current manual methods employ a receptacle/tank to develop the gel aided by the use of a plastic scooper to transfer and hold the gel when exchanging the solution. The gels are frequently damaged during development and transfer using a scooper. Gel developing apparatuses such as U.S. Pat. No. 4,750,506 avoids direct handling of the gels by the use of cassettes to hold the gel within an outer tank. The problem lies with the cassettes which are intended to hold the gels in a vertical position during development. Gravity can cause the gels to slide down and lie undesirably folded at the bottom of the cassette. Furthermore, the cassettes equipped with the fluid permeable mesh to hold the gels in place require the gels to be of a certain thickness; too thick and the mesh can cause damage on the gel surface, too thin and the gel can slide down and fold up at the base of the cassette. The stacking arrangement of the cassettes also impairs visual monitoring of the gels. A gel destaining apparatus disclosed in U.S. Pat. No. 4,702,266 places gels in between horizontally stacked trays. For the purposes of destaining, the gels within do not have to be chronically monitored, however, for the purposes of gel staining and development, this stacking arrangement would greatly impair and obstruct visualization of the gels. A dish washing apparatus disclosed in U.S. Pat. No. 898,354 uses a submergible inner tray with openings for holding dishes within the outer tank. This inner tray functions to hold dishes within the closed dish washing apparatus. Furthermore, the base of the tray is not detachable and the apparatus is intended more towards washing dishes and not developing fragile electrophoresis gels. A tool decontamination apparatus disclosed in U.S. Pat. No. 4,630,625 has an inner chamber with openings along the floor. This inner chamber is positioned within the cabinet near the opening by the means of latches. Again, the inner chamber does not have a removable base and the chamber is positioned to facilitate a washing process with unwanted debris exiting through the openings and settling at the base of the cabinet.

Two other gel developing apparatuses claimed in U.S. Pat. No. 5,112,957 and 4,391,689 involve sophisticated systems which automatically dispense fixing, staining, and rinsing solutions as well as monitoring the development time. Such automated systems are expensive and arguably cumbersome for developing gels that require manual attention.

The present invention relates to an apparatus and method to develop gels efficiently with minimal contact of the gels of interest. The multi-tank gel developing apparatus can develop multiple gels in separate inner tanks which have openings above the base along the side walls which allow circulation of fluids with the inner and outer tanks. By lifting the inner tanks out and above the outer tank, the solution within the inner tanks can be drained. The remaining solution in the outer tank can be decanted and exchanged with a new solution. Afterwards, the inner tanks holding the gels of interest can be re-immersed into the outer tank for further processing and development.

BRIEF SUMMARY OF THE INVENTION

The claimed invention is a multi-tank/receptacle made of plastic for the purpose of electrophoresis gel development processes such as silver staining or dyes staining. This multi-tank method comprising of two inner tanks within a larger outer tank allows for the exchange of developing solutions without the need to directly handle the gels, thereby minimizing damages of the gels. Each of the inner tanks can accommodate at least one slab or tube gel made of polyacrylamide or agarose. The tanks are not limited by the chemical composition of the gels nor by the gel thickness. The numerous openings along the lower portion of the side walls of the inner tanks (FIG. 2) allow the solution to freely circulate between the inner and outer tanks. The solution inside the apparatus is exchanged by lifting and draining the inner tanks which retain the gels inside. The remaining solution in the outer tank is exchanged with a new solution and the inner tanks are then re-immersed into the outer tank. The bottoms of the inner tanks are easily removable by pushing the corner tabs shown on FIGS. 2 and 3. This removable base allows the gel to be easily transferred to a viewing light table or a drying apparatus after the development process has been completed. Physical damage often incurred by the use of scoopers etc., are avoided by the use of the claimed multi-tank gel developing apparatus. Furthermore, gels are developed in a flat horizontal position thereby, facilitating visual observation of the gels during development.

DETAILED DESCRIPTION OF THE CLAIMED APPARATUS

Figure 1:
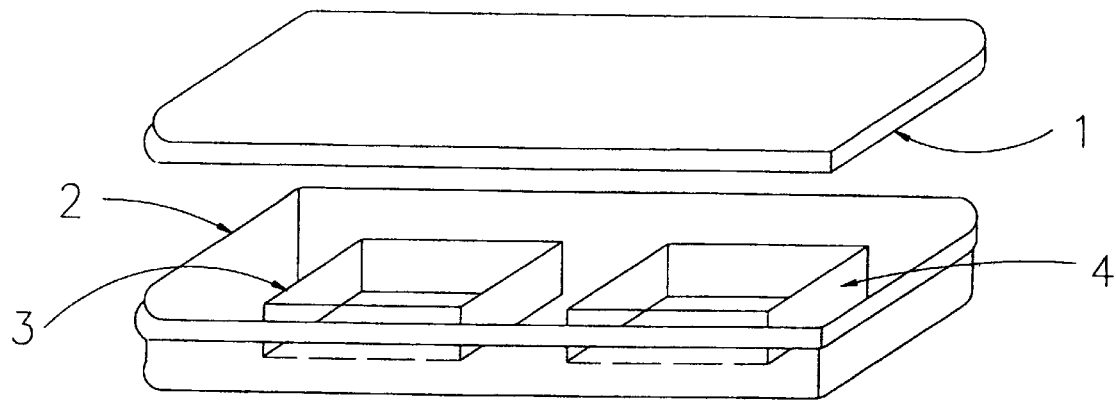
FIG. 1 is an exploded perspective view of the claimed apparatus.
Figure 2:
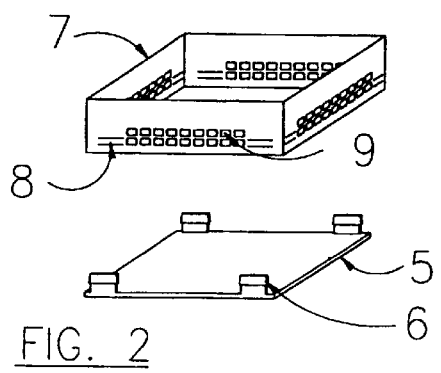
FIG. 2 is a close up of one of the two inner tanks showing the base detached from the tank walls.
Figure 3:
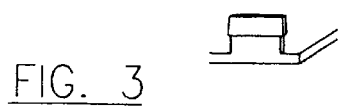
FIG. 3. is a close up of one of the four tabs on the removable base.
Figure 4:
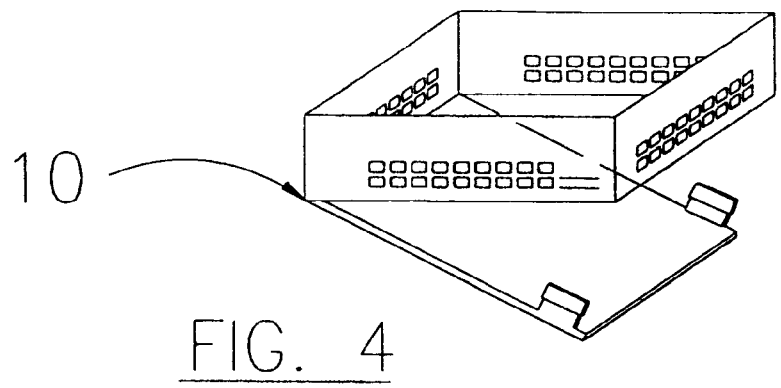
FIG. 4 is another embodiment of the removable base with one edge pivotally hinged or made into a continuous flap.
Figure 5:
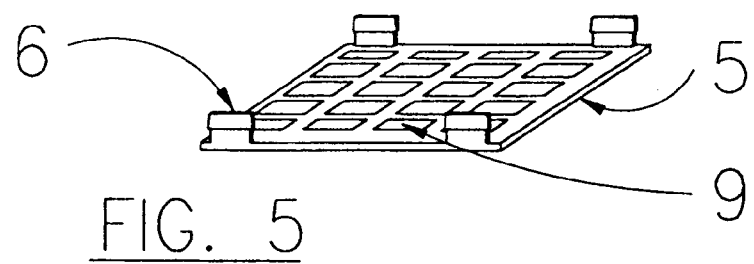
FIG. 5 shows another embodiment of the base with openings along the floor.
Figure 6:
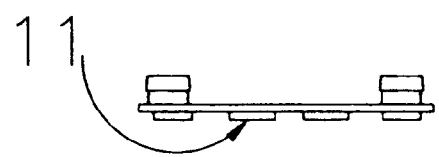
FIG. 6 is a side profile view of the unattached base.
Figure 7:
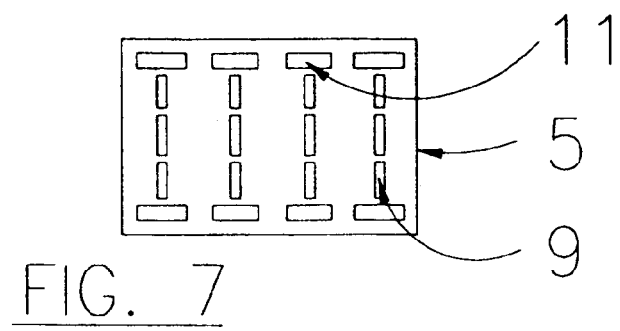
FIG. 7 shows the bottom side of the inner tank with spacers along two opposite edges and openings along the base.

The apparatus shown in FIGS. 1–3 comprises of three tanks, one large outer and two inner tanks. 2 shows the outer tank. 3 and 4 shows the two inner tanks. 1 is the transparent protective lid which can be used to cover the apparatus during the development process. The openings 9 located slightly above the base of the inner tanks allow the various solutions to circulate freely with the outer tank. The flat horizontal arrangement of the inner tanks 3 and 4 disposed within an outer tank 2 minimizes the amount of solution required to fully soak the gels as well as allowing the gels to be visually monitored. At least two gels can be simultaneously developed with the present apparatus. Solutions are exchanged by simply lifting the two inner tanks outside of the outer tank 2. The solution within the inner tanks 3 is drained out through the openings 9 while the gels remain inside the inner tanks 3 and 4. The remaining solution in the outer tank 2 can be poured out and exchanged with a new or different solution. Then, the two inner tanks 3 and 4 with the gels disposed within can be re-immersed into the outer tank. The solution level should be slightly above the openings 9 of the inner tanks 3 and 4. Sufficient space exists between the two inner tanks and the outer tank to allow movement or shaking when the apparatus is used in conjunction with a shaking table. The gels remain within the confines of the inner tanks 3 and 4 while the solution communicates between the inner and outer tanks. The use of the lid 1 is optional and is not required. The lid 1 can be used when leaving the apparatus unattended or for storage purposes. The apparatus can be placed on a shaking table or shaken by hand to facilitate circulation of the solution within the apparatus. FIG. 2 shows a close up of one of the inner tanks with the base detached from the upper walls. The inner tanks 3 and 4 are made with detachable bases. 5 shows the base portion of the inner tank. 6 is one of the four corner push tabs used to hold the base to the side walls 7 of the inner tank. 8 shows the insertion point for the tabs which hold the base to the walls. The corner tabs 6 can be used to detach the base and easily slide the gel to a light table or drying apparatus. FIG. 4 shows a different embodiment of the removable base where one end is pivotally hinged by means of a continuous flap or hinge 10 so the base can move away or towards the tank walls 7, thereby attaching or partially detaching the base from the inner tank walls 7. FIG. 5 shows another embodiment of the detachable base with openings 9 along the floor of the base. The base spacers 11 as shown in FIGS. 6 and 7 provide sufficient space between the floor of the outer tank 2 and the bottom of the inner tanks, thereby allowing solutions to communicate therethrough the bottom of the inner tanks in addition to the side wall openings 9.

The present apparatus can be used for several other gel processes such as gel destaining, but the apparatus is most suited for methods of staining and gel development because the development of an image thereon a gel requires constant monitoring. The inner and outer tanks can be easily cleaned of stains or dyes.

The material to construct the apparatus is not critical. Any inert, plastic type of material especially those suitable for machining, injection molding or other common means of manufacturing may be used. Clear or opaque plastic is preferred since stains and dye marks are easily noticeable.

The convenience and uniqueness of the multi-tank gel developing apparatus will be readily apparent to those skilled in the area of gel electrophoresis and gel development. Although modifications such as the use of materials and components in addition to their configurations maybe applied to the invention, the fundamental spirit and scope of the present invention will be apparent as set forth in the following appended claims. (8 claims)

What is claimed is:

1. An apparatus comprising:
   a. an outer tank comprising a base and upstanding-walls disposed therearound wherein fluid is introduced therein:
   b. an open top inner tank positioned within said outer tank having a detachable base and upstanding walls disposed therearound and openings disposed in said walls or base;
   c. means of securing said inner tank base to said inner walls such that the inner tank base can be removed or attached to the inner tank walls; and
   d. an electrophoretic gel to be treated disposed in said inner tank base wherein processing fluid is disposed in said outer tank and communicates through said openings to treat said gel electrophoretic gel whereinafter, the inner tank is removed from said outer tank, and inner tank base is removed from said inner tank walls to access the treated electrophoretic gel therein.

2. The apparatus according to claim 1, wherein said openings disposed on said upstanding walls of said inner tank comprise at least ten percent of the area of said inner tank walls.

3. The apparatus according to claim 2, wherein said openings are disposed above said inner tank base.

4. The apparatus according to claim 3, wherein openings are disposed on said inner tank base and comprise at least ten percent of the area of said tank base.

5. The apparatus according to claim 4, wherein said inner tank base further comprises spacing elements disposed beneath, proximate to the outer area, thereby creating a space permitting said fluid to communicate and circulate therethrough from the outer tank to the inner tank and vise versa.

6. The apparatus according to claim 1, wherein said securing means comprise tabs that attach said inner tank base to said inner tank walls and upon depression of said tab, the inner base is removed from said inner tank walls.

7. The apparatus according to claim 1, wherein said securing means comprise a hinge means to secure one end of said inner tank base to adjacent said tank wall such that the tank base pivots side to side along the axis of the hinge.

* * * * *